United States Patent [19]

Caldwell et al.

[11] 4,427,782

[45] Jan. 24, 1984

[54] **ISOLATION OF PRINCIPAL OUTER MEMBRANE PROTEIN AND ANTIGEN OF *CHLAMYDIA TRACHOMATIS***

[76] Inventors: Harlan D. Caldwell, 821 Parker Ave., Hamilton, Mont. 59840; Julius Schacter, 17 Channel Dr., Corta Madera, Calif. 94925

[21] Appl. No.: 240,223

[22] Filed: Mar. 3, 1981

[51] Int. Cl.$^3$ .................. G01N 33/56; G01N 33/58; G01N 33/60; C07G 7/00
[52] U.S. Cl. .................................. 436/542; 436/543; 436/544; 436/545; 436/546; 436/547; 435/7; 260/112 R; 260/112 B
[58] Field of Search .................. 424/1, 12, 85, 88; 260/112 R, 112 B; 435/7; 436/542–547

[56] References Cited

U.S. PATENT DOCUMENTS 4,118,469 10/1978 Caldwell et al. .................. 424/1

OTHER PUBLICATIONS

Taylor-Robinson et al., Lancet, 2 Jun. 1979, pp. 1162–1163.
Schuller et al., Lancet, 6 Jan. 1979, pp. 19–20.
Banks et al., Infection and Immunity, vol. 20, 1978, pp. 864–866.
Caldwell et al., Infection and Immunity, vol. 31, 1981, pp. 1161–1176.
Caldwell et al., J. Immunol., vol. 115, 1975, pp. 969–975.
Caldwell et al., J. Immunol., vol. 118, 1977, pp. 437–441.
Caldwell et al., J. Immunol., vol. 118, 1977, pp. 442–445.

*Primary Examiner*—Christine M. Nucker
*Attorney, Agent, or Firm*—Phillips, Moore, Lempio & Finley

[57] ABSTRACT

Procedures are presented for isolating the major outer membrane protein of *Chlamydia trachomatis*. The isolated protein is a species specific antigen which comprises about 60% of the *C. trachomatis* cell outer membrane structure. The protein has a molecular weight ranging from about 38,000 to 44,000 daltons, with a mean molecular weight of about 39,500 daltons. The protein antigen is purified from *C. trachomatis* cells by first extracting the cell contents with a mild anionic detergent, preferably sarcosyl, to leave a residue of intact outer cell membranes. These outer cell membranes are then extracted with a strong anionic detergent, preferably sodium dodecyl sulfate, which solubilizes the 39,500 dalton antigen. The antigen is then purified by hydroxlapatite chromatography. The antigen is species specific for *Chlamydia trachomatis* and may be utilized in assaying Chlamydial infection in mammals.

19 Claims, No Drawings

ISOLATION OF PRINCIPAL OUTER MEMBRANE PROTEIN AND ANTIGEN OF CHLAMYDIA TRACHOMATIS

The invention described herein was made in the course of, or under, a grant from the National Institutes of Health.

TECHNICAL FIELD

This invention relates generally to the isolation of cell protein of microorganisms which exhibit antigenic properties and more particularly to the isolation of the principal outer membrane protein of *Chlamydia trachomatis*, which protein exhibits antigenic properties common to all the *Chlamydia trachomatis* serotypes.

BACKGROUND OF THE INVENTION

*Chlamydia trachomatis* is one of the two microorganism species of the genus Chlamydiaceae, order Chlamydiales. The other species is *Chlamydia psittaci*. *Chlamydia trachomatis* in its some 15 various strains, are the etiologic agents for a number of human ocular and genital diseases including trachoma, inclusion, conjunctivitis, lymphogranuloma venereum, "nonspecific" or non-gonococcal urethritis and proctitis. *C. trachomatis* infection is pervasive throughout the general population. It has been estimated, for instance, that *C. trachomatis* is accountable for several million cases per year of nongonococcal urethritis.

Since *C. trachomatis* mediated disease is widespread, a reliable, simple and inexpensive test for the organism's presence is highly desirable and of great importance so that proper treatment may be undertaken. The only serological test in current use is the microimmunofluoresence test. This test however requires that the strains of *C. trachomatis* be used as serological test antigen. In addition, the facilities for conducting this test are available in only a limited number of laboratories throughout the world. The test is very laborious, time consuming and difficult to perform.

Recently, U.S. Pat. No. 4,118,469, noted the preparation of an antigen of *C. trachomatis* useful in serological testing for lymphogranuloma venereum and nongonoccocal urethritis. Such antigen was purified from *C. trachomatis* organisms by immunoadsorption chromatography using the monospecific antiserum as a specific ligand covalently bound in an agarose gel column. This antigen had a molecular weight of about 160,000 daltons, and in counter-immunoelectrophoresis testing was capable of detecting antibodies from the sera of lymphogranuloma venereum patients. However, when utilized in a similar test with sera of non-gonoccocal urethritis patients, this antigen failed to detect antibodies. It was successful, however, in detecting antibodies in two dimensional immunoelectrophoresis testing.

In any event, however, there is still great medical interest in the isolation of species specific antigens of *C. trachomatis* which are capable of the detection of *C. trachomatis* infection, preferably by commonly practiced antigen-antibody assay methods.

BRIEF SUMMARY OF THE INVENTION

The present invention presents a species specific antigen which comprises the principal outer membrane protein of *Chlamydia trachomatis*. Such protein comprise about 60% of the total associated outer membrane protein of *C. trachomatis*, and have a size or subunit molecular weight of between 38,000 and 44,000 daltons, with a mean molecular weight of 39,500 daltons. Hereinafter for ease in reference, this principal outer membrane protein group will be referred to as MP 39.5 signifying "major outer membrane protein having a mean subunit molecular weight of 39,500 daltons".

When tested against *C. trachomatis* antibodies derived from all the serotypes thereof, MP 39.5 reacts with species specificity. Thus MP 39.5 is a *C. trachomatis* species specific antigen. MP 39.5 is a unique protein common to all *C. trachomatis* serotypes, and as an antigen provides a basis for the identification of all the *C. trachomatis* serotypes.

MP 39.5 is isolated from *C. trachomatis* elementary bodies, i.e., the intact microorganism cells, by first growing suitable strains of the organism and collecting the elementary bodies free from the growth medium. The purified elementary bodies are treated by means hereinafter described to isolate the outer cell membranes. These outer cell membranes are selectively separated from the cell cytoplasm membrane and protoplasm. The isolated outer cell membranes are then further treated by a method hereinafter described to yield essentially pure MP 39.5.

The MP39.5 recovered from the outer membranes is then available for either (1) direct reaction with *C. trachomatis* antibodies generated in the serum of *C. trachomatis* infected hosts; or (2) to be injected into laboratory animals to produce antiserum against MP39.5. Thus the recovered MP39.5 may be utilized in immunodiagnostic assay procedures for *C. trachomatis.*

It is therefore an object of the invention to provide the principal outer membrane protein (MP39.5) of *Chlamydia trachomatis.*

It is another object of the invention to provide a *C. trachomatis* species specific antigen.

It is yet another object of the invention to provide a method for isolating *C. trachomatis* principal outer membrane protein.

It is still another object of the invention to provide an antigen suitable for assaying chlamydial infection.

Other objects and advantages of the invention will be apparent from a review of the following description and the claims appended hereto.

DETAILED DESCRIPTION OF THE INVENTION

MP39.5 is the principal outer membrane protein of *C. trachomatis* and it is species specific antigen to all *C. trachomatis* serotypes.

isolation of MP39.5 from *C. trachomatis* elementary bodies is accomplished by an essentially two step extraction procedure. In the first step, purified elementary bodies are contacted with an aqueous solution of a mild anionic sarcosine detergent, preferably sodium N-lauroyl sarcosine (commonly referred to as sarcosyl). The sarcosyl selectively dissolves out the elementary body cytoplasm including the protein, nucleic acids and other molecular structures associated therewith, leaving the elementary body outer membrane as an insoluble residue.

Electron microscopic studies indicate that the sarcosyl treatment leaves an insoluble residue which consists of uniform particles of single intact double-track unit membranes of a size and morphology characteristic of native chlamydial elementary body outer membrane.

In the second process step, the residual elementary body membranes are lysed with a strong anionic detergent, preferably sodium dodecyl sulfate, which solubilizes the principal outer membrane protein, MP39.5. The MP39.5 is then recovered from the detergent solution, and purified to yield the MP39.5 antigen.

The purified MP39.5 protein, when tested against antibody derived from known *C. trachomatis* serotypes demonstrates that MP39.5 is a species specific antigen of *C. trachomatis* organisms.

The entire and detailed isolation procedure and characterization of MP39.5 as a *C. trachomatis* antigen may be best understood from a review of the following detailed procedures and tests:

Growth and purification of *C. trachomatis* organisms.—The following *C. trachomatis* strains were used: L2/434/Bu(L2), E/UW-5/Cx(E) and C/TW-3/OT(C). Chlamydiae were grown in HeLa 229 cells as described previously in the publication in October of 1975 in the Journal of Immunology v. 15, pgs 963–968 by Caldwell et.al., entitled "Antigenic Analysis of Chlamydiae by Two-Dimensional Immunoelectrophoresis." Such disclosure is incorporated herein by reference. The L2 strain was also grown in suspension cultures of L-929 cells. L-cell-propagated L2 organisms were used for the isolation and purification of the 39,500 dalton protein.

Chlamydiae were harvested from HeLa cell monolayers grown in 150 $cm^2$ polystyrene culture flasks (Corning Glass Works, Corning, N.Y.) with 90% of the cells containing inclusions at 48 hours postinoculation. Medium was poured off and cells were removed with 4 mm glass beads and 10 ml of cold Hanks' balanced salt solution. These cell suspensions were pooled and the cells ruptured by sonication (Braunsonic Model 1510). This suspension was centrifuged at 500×g for 15 min at 4° C. The supernatants were layered over 8 ml of a 35% Renographin solution (v/v) (diatrizoate meglumine and diatrizate sodium, 76% for injection, Squibb and Sons, N.Y.) in 0.01 M N-2-hydroxyethylpiperazine-N'-2-ethanesulfonic acid containing 0.15 M NaCl. They were then centrifuged at 43,000×g for 1 hour at 4° C. in an SW 27 rotor (Beckman Instruments Inc., Fullerton, Ca). The pellets were resuspended in 0.01 M sodium phosphate (pH 7.2) containing 0.25 M sucrose and 5 mM L-glutamic acid (SPG). pooled and layered over discontinuous Renographin gradients (13 ml of 40%, 8 ml of 44% and 5 ml of 52% Renographin, v/v). These gradients were centrifuged at 43,000×g for 1 hour at 4° C. in an SW 27 rotor.

The Chlamydiae elementary body bands, located at the 44/52% Renographin interface, were collected, diluted with three volumes of SPG and then centrifuged at 30,000×g for 30 min. The elementary body pellets were washed in SPG to remove residual Renographin. The purified elementary bodies were resuspended in SPG and stored at −80° C. The purity of the elementary body preparations was determined by electron microscopy and Macchiavello stained smears.

Isolation of chlamydial outer membrane complexes (COMC) by sarcosyl extraction of intact elementary bodies.—*C. trachomatis* L2 elementary bodies as collected above were suspended (approximately 5 mg protein/ml) in 5 ml of phosphate buffer solution (PSB) comprising 0.01 M sodium phosphate, and 0.15 M Nacl, pH 8.0, also containing 2% sarcosyl and 1.5 mM ethylenediaminetetracetic acid (EDTA). This suspension was incubated at 37° C. for 1 hour and then centrifuged at 100,000×g for 1 hour. The insoluble pellet was resuspended in the same sarcosyl buffer and centrifuged as before. The pellet was washed twice in PBS to remove excess detergent and then resuspended in 0.02 M sodium phosphate, pH 8.0, containing 19 mM $MgCl_2$ and 25 g/ml deoxyribonuclease (Worthinton Biochemical Corp., Freehold, N.J.) and ribonuclease (Millipore Corp., Freehold, N.J.). This suspension was then incubated for 2 hours at 37° C., centrifuged and the insoluble pellet washed twice with PBS to remove any remaining nucleases. This sarcosyl insoluble material consisted of chlamydial outer membrane complexes (COMC).

Purification of the 39,500 dalton outer membrane protein.—Isolated COMC prepared from 25–30 mg L2 EB protein in the procedures as noted above, was suspended in 5 ml of 2% sodium dodecyl sulfate buffer and incubated at 37° C. for 1 hour. This suspension was centrifuged at 100,000×g for 1 hour and the soluble supernatant fraction collected.

This sodium dodecyl sulfate extract, enriched in the 39.500 dalton protein, was then dialyzed against 200 volumes of 0.01 M sodium phosphate, pH 6.4, containing 1 mM dithiothreitol (DTT) and 0.1% sodium dodecyl sulfate (column equilibration buffer) for 24 hours with several changes of dialysate. This extract was fractionated by hydroxylapatite chromatograpy in the presence of sodium dodecyl sulfate using the technique disclosed by Moss and Rosenblum in J. Bio. Chem., 1972, V. 247, pgs. 5194–5198.

Briefly, the dialyzed extract (8–10 ml) was supplied to a pre-equilibrated hydroxylapatite column (0.9×30 cm). The column was washed with 100 ml of equilibration buffer and eluted with a 150 ml linear gradient of 0.1 M to 0.6 M sodium phosphate, pH 6.4, containing 1 mM DTT and 0.1% sodium dodecyl sulfate. The column eluate was collected in 40 drop fractions at a flow rate of 5–6 ml per hour and spectrophotometrically monitored at 280 nm absorbence. Those fractions showing positive absorbence were analyzed by sodium dodecyl sulfate-polyacrylamide gel electrophoresis.

The polyacrylamide gels were stained with Coomassie blue for protein and Stains-All to detect nucleic acid and glycolipid moieties. The phosphate molarity of every tenth column fraction was determined by measuring total phosphorous and converting to phosphate molarity by using a standard curve prepared wiht known sodium phosphate standards. Those fractions that contained only the MP39.5 were pooled and concentrated to a 1–2 ml volume by vacuum dialysis against 0.05 mM Tris-HCl, pH 8.5, containing 0.15 M NaCl and 0.1% sodium dodecyl sulfate. These concentrated preparations were used for performing analytical assays to test for protein purity and as a source of immunogen for the preparation of antisera in laboratory animals.

It will be understood that the detergent extraction temperatures and times noted in the procedures above may be varied from those as stated. It is perfectly feasible to extract at higher temperatures e.g., 45° C., 60° C., 80° C., or even 100° C. Higher extraction temperatures may be accompanied by shorter extraction times. For instance, extraction at 100° C. for 10 minutes, is sufficient to solubilize essentially all the elementary body components which are soluble in the particular detergent. Generally speaking, however, if time is not a problem, it is desirable to extract at the lower temperatures, e.g., 37° C., in order to avoid any chance of denaturing the desired proteins.

The molecular weights of the purified COMC proteins were determined by polyacrylamide gel electrophoresis. Specifically, the Chlamydial proteins were electrophoresed on 12.5% acrylamide slab gels in the discontinuous Tris (hydroxymethyl) aminomethane-glycine (Trisglycine) system described by Laemmli in Nature (London) v. 227, pgs. 680-685 (1970). The ratio of acrylamide to N, N'-methylenebisacrylamide was 30:0.8 in both the 12.5% separating gel and 5% stacking gel. Before electrophoresis samples were mixed with an equal volume of solubilizing solution (0.1 M Tris HCl, pH 6.8), containing 2.5% sodium dodecyl sulfate (BDH Chemicals Ltd.), 5% 2-mercaptoethanol, 20% glycerol and 0.0001% bromophenol blue and boiled for 10 min. Electrophoresis in Tris-glycine buffer (ph 8.6) containing 0.1% sodium dodecyl sulfate was carried out at a constant current of 25 mA. Gels were stained in 0.25% Coomassie brilliant blue R-250 in 7% acetic acid and 30% methanol. The protein standards used for estimating chlamydial protein molecular weights were: phosphorylase b (94,000), bovine serum albumin (67,000), ovalbumin (43,000), carbonic anhydrase (30,000), soy bean trypsin inhibitor (20,100) and α-lactalbumin (14,400) (Pharmacia, Inc., Piscataway, N.J.).

In one experimental study approximately 1.4 mg of purified MP39.5 protein was recovered after concentration, after following the procedures set forth above. Although the amount recovered was small compared to the recovery of outer membrane proteins from more readily cultivatable microorganisms, the yield was quite exceptional considering that only 25-30 mg. of elementary body protein was used as the starting material.

Preparation of Antisera—Swiss Webster mice strain 1CR (Charles River Co. Baltimore, MD) were immunized subcutaneously on day 0 with 30 μg of purified Mp39.5 emulsified with Freund's incomplete adjuvant. Immunizations were repeated with the same amount of purified protein administered subcutaneously without adjuvant on days 16 and 27. Mice were bled by cardiac puncture 5 days after each immunization (days 21 and 32, respectively). The reactivity and specificity of the pooled sera collected from each bleeding was evaluated by indirect immunofluorescence.

Table 1, below, presents the results of tests against elementary bodies of the various Chlamydiae serotypes (both trachomatis and psittaci) with the mouse generated antisera.

TABLE I

Indirect immunofluorescence of Chlamydia with mouse antiserum prepared against purified MP39.5

| Organism | Serotype or strain | Reciprocal antibody titer of mouse* anti-MP39.5 | |
|---|---|---|---|
| | | Titer after 2nd immunization (day 21) | Titer after 3rd immunization (day 32) |
| C. trachomatis | A | — | — |
| | B | — | — |
| | Ba | 8 | 128 |
| | C | — | — |
| | D | 8 | 128 |
| | E | 8 | 64 |
| | F | — | — |
| | G | — | — |
| | H | — | — |
| | I | — | — |
| | J | — | — |
| | K | 8 | 128 |
| | L1 | 8 | 128 |
| | L2 | 64 | 512 |
| | L3 | 8 | 128 |
| | Mouse pneumonitis | — | — |
| C. psittaci | 6BC | — | — |
| | Feline pneumonitis | — | — |
| | Guinea pig inclusion conjunctivitis | — | — |

*Highest dilution of antiserum (starting at 1:8) showing fluorescence. Serum antibody titers are IgG only, no fluorescence was observed with anti-IgM specific conjugate.

In a procedure similar to that noted for the production of antiserum in mice, rabbits were inoculated with 300 μg each of purified MP39.5 protein. The protein was injected intramuscularly, and the rabbits were then bled after a suitable time was allowed for induction of the MP39.5 antibodies. The pooled rabbit sera was then utilized for evaluation for reaction against all the various Chlamydeae elementary body serotypes. The results of these tests are set forth in Table 2, below.

TABLE II

Indirect fluorescent antibody staining of intact Chlamydeae with rabbit antiserum raised against the major outer membrane protein MP39.5 of the L2 C. trachomatis strain.

| Organism | Serotype | Reciprocal Fluorescent Antibody Titer |
|---|---|---|
| C. trachomatis | A | 64 |
| | B | 4096 |
| | Ba | 8192 |
| | C | 64 |
| | D | 512 |
| | E | 4096 |
| | F | 2048 |
| | G | 4096 |
| | H | 256 |
| | I | 64 |
| | J | 256 |
| | K | 4096 |
| | L1 | 128 |
| | L2 | 8092 |
| | L3 | 4096 |
| C. psittaci | 6BC | <8 |
| | Mn | <8 |
| | Feline pneumonitis | <8 |
| | Guinea pig inclusion conjunctivitis | <8 |

Fluorescence was determined by reacting elementary bodies of each Chamydia serotype with serial 2-fold dilutions of rabbit anti-MP39.5 (L2 antiserum). Note that anti-MP39.5 reacts with every C trachomatis serotype but not with the C. psittaci strains. These results show that MP39.5 is a C. trachomatis species specific antigen.

When MP39.5 protein prepared from other C. trachomatis serotypes, e.g. H, was utilized to generate antisera in laboratory animals, and the resultant antisera was reacted with elementary bodies of all the C. trachomatis serotypes, positive results similar to those set forth in Table II above were obtained.

In any event, however, it is clear that the MP39.5 antigen has species specificity against all the C. trachomatis serotypes.

As noted above monospecific antibodies against MP39.5 antigen can be generated by suitable inoculation procedures with laboratory animals such as mice and/or rabbits. The animal generated antibodies may be utilized in assays for Chlamydial infection in other mammals. These assays may be conducted in well known procedures for assaying the presence of bacterial antigen in the infected subject. Once a supply of monospecific antibodies has been secured from MP39.5 antigen inoculated laboratory animals, either direct or indirect assay procedures can be undertaken with specimens secured from mammals suspected of harboring Chlamydial infections.

Assay techniques such as enzyme linked immunoabsorbent assays (ELISA) or radioimmune assays (RIA) are suitable for these purposes.

In a direct assay procedure monospecific antibody against the MP39.5 protein may be covalently or non-covalently attached to a solid phase support system. As is customary in these techniques the support system may be glass, plastics and the like. The solid phase support with attached monospecific antibody against MP39.5 may be incubated with a specimen previously secured from the individual suspected with having Chlamydial infection. Prior to incubation, the specimen is treated with a detergent such as sodium dodecyl sulfate or other anionic, nonionic or cationic detergent to extract the MP39.5 outer membrane antigen from any Chlamydial organisms which may be present therein. It is the extracted specimen which is incubated with the solid phase support.

Monospecific antibody against MP39.5 antigen, which has been previously radiolabeled or conjugated with enzyme by known techniques, is then equilibrated against the support system. Any MP39.5 antigen present in the specimen and which had been bound to the antibody on the support system will in turn bind to the radiolabeled or enzyme conjugated antibody.

If radiolabeled antibody is used, the amount of residual radioactivity in the sample may then determined. This value is compared to specimens that have been determined to be free of Chlamydial MP39.5 antigen. In the event enzyme conjugated antibody is used, a substitute specific for the enzyme is added to the solid support reaction mixture and the resultant color change is recorded spectrophotometrically. This color change is compared to samples known to be free of Chlamydial MP39.5 antigen.

Thus the presence of MP39.5 antigen is mammalian specimens can be assayed directly.

Alternatively, indirect assay procedures can be used. specifically, the Chlamydial (MP39.5) antigen secured as in the procedures set forth above, may be covalently or non-covalently bound to a suitable solid phase support system. A specimen from the individual suspected of having Chalmydial infection is treated with detergent, e.g., sodium dodecyl sulfate to extract the major outer membrane protein antigen from any *C. trachomatis* cells which may be present.

The extract from the specimen may then be mixed with a known quantity of radiolabeled or enzyme conjugated antibody against the MP39.5 antigen, previously secured from a laboratory animal source. The specimen extract—antibody mixture may then be incubated with the solid support system and its bound MP39.5 antigen.

The radioactivity of the solid support system is measured; or color development in the enzyme conjugated system is measured; and compared to specimens similarly treated as standards and which do not contain any Chlamydial antigen.

The ability of the clinical sample suspected of containing *C. trachomatis* to inhibit the ability of the radiolabeled or enzyme conjugated antibodies to the MP39.5 antigen bound to the solid support thus reveals the presence, or absence, of the MP39.5 antigen in the clinical specimen. Any demonstrated inhibition indicates the presence of *C. trachomatis* infection.

Other suitable assay method and variations will be apparent to those skilled in such assay techniques.

We claim:

1. As a species specific antigen for *Chlamydia trachomatis*, the principal outer membrane protein of *Chlamydia trachomatis* micro-organisms having a molecular weight ranging from about 38,000 to 44,000 daltons.

2. The species specific antigen of claim 1 wherein the antigen has a mean molecular weight of about 39,500 daltons.

3. A method for isolating a species specific protein antigen of *Chlamydia trachomatis* comprising separating the outer cell membrane material of *Chlamydia trachomatis* micro-organisms from the remainder of the cell contents, and then contacting said separated outer cell membrane material with a strongly anionic detergent to solubilize the protein antigen, and thereafter recovering the protein antigen from the detergent solution, and purifying the protein antigen.

4. The method of claim 3 wherein the purified protein antigen has a molecular weight of between about 38,000 and 44,000 daltons.

5. The method of claim 4 wherein the protein antigen has a mean molecular weight of about 39,500 daltons.

6. The method of claim 3 wherein the remainder of the cell contents are solubilized by contacting elementary bodies of *Chlamydia trachomatis* with a mild anionic detergent and in which the outer cell membrane is essentially insoluble.

7. The method of claim 6 wherein the mild anionic detergent is a sarcosine detergent.

8. The method of claim 7 wherein the sarcosine detergent is sodium N-lauroyl sarcosine.

9. The method of claim 3 wherein the separated outer cell membrane is contacted with a salt of an alkyl sulfate detergent to solubilize the protein antigen.

10. The method of claim 9 wherein the salt of an alkyl sulfate detergent is sodium dodecyl sulfate.

11. The method of claim 9 wherein the solubilized protein antigen is purified by hydroxylapatite chromatography.

12. A method for assaying the presence of Chlamydial infection in a mammal comprising generating antibodies against the principal outer membrane protein antigen of *Chlamydia trachomatis* which outer membrane protein has a mean molecular weight of about 39,500 daltons, securing a specimen from a mammal suspected of having a *Chlamydia trachomatis* infection, treating said specimen to solubilize any Chlamydia outer cell membrane protein having a molecular weight of about 39,500 daltons which may be present in said specimen, securing an amount of the generated antibodies, contacting the antibodies with said solubilized specimen, and determining any reaction between said antibodies and said solubilized specimen.

13. The method of claim 12 wherein the assay method is a radioimmune assay.

14. The method of claim 12 wherein the assay method is an enzyme linked immuno absorbent assay.

15. A lyophilized composition containing *Chlamydia trachomatis* outer membrane protein having a mean molecular weight of about 39,500 daltons.

16. Antisera compositions useful in immuno diagnostic assays of *Chlamydia trachomatis* infection in mammals, said compositions being recovered from the blood serum of animals which have been previously inoculated with the principal outer membrane protein of *Chlamydia trachomatis*, said protein having a mean molecular weight of about 39,500 daltons.

17. The method of claim 12 wherein the chlamydial antibodies are generated by introducing *Chlamydia trachomatis* antigen into hosts to induce the production of antibodies against the *Chlamidia trachomatis* principal outer membrane protein having a mean molecular weight of about 39,500 daltons, and thereafter recovering the antibodies from said hosts.

18. The method of claim 12 wherein said specimen is treated to solubilize any *Chlamydia trachomatis* outer cell membrane protein present in said specimen.

19. Antibodies possessing a specific affinity for *Chlamydia trachomatis* principal outer cell membrane proteins having mean molecular weights of about 39,500 daltons.

* * * * *